(12) United States Patent
Charles et al.

(10) Patent No.: US 9,499,639 B2
(45) Date of Patent: Nov. 22, 2016

(54) LPS EXTRACTION PROCESS

(71) Applicant: GlaxoSmithKline Biologicals S.A., Rixensart (BE)

(72) Inventors: Philippe Charles, Rixensart (BE); Geoffroy Geldhof, Rixensart (BE); Vincent Mancuso, Rixensart (BE)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 14/592,894

(22) Filed: Jan. 8, 2015

(65) Prior Publication Data

US 2015/0126727 A1 May 7, 2015

Related U.S. Application Data (62) Division of application No. 13/698,937, filed as application No. PCT/EP2011/058016 on May 18, 2011, now abandoned.

(30) Foreign Application Priority Data

May 20, 2010 (GB) .................................. 1008401.0

(51) Int. Cl.
*C08B 37/00* (2006.01)
*C12P 19/04* (2006.01)
*C07H 1/00* (2006.01)
*C09K 3/00* (2006.01)

(52) U.S. Cl.
CPC ............. *C08B 37/0003* (2013.01); *C07H 1/00* (2013.01); *C09K 3/00* (2013.01); *C12P 19/04* (2013.01)

(58) Field of Classification Search
None
See application file for complete search history.

(56) References Cited

FOREIGN PATENT DOCUMENTS

GB 2220211 A * 1/1990 ........... A61K 31/715

OTHER PUBLICATIONS

Galanos, European J. Biochem. 9 (1969) 245-249.*

* cited by examiner

*Primary Examiner* — Layla Berry
(74) *Attorney, Agent, or Firm* — Joseph J. Schuller; Jason C. Fedon (57) ABSTRACT

The present invention provides a method of lipopolysaccharide (LPS) extraction from gram negative bacterial cells comprising the step: extracting LPS from the cell culture in a composition (LPS extraction composition) comprising water, an alcohol and a further organic solvent.

12 Claims, 6 Drawing Sheets

Figure 1 : Kinetic of extraction from cell broth 101B at 50°C

Figure 2: Reproducibility data from broth 101B

Figure 3A: Distribution of extraction yields of 80 experiments with 0% water

NORMAL distribution without water µ=6.5%, s=2.7
N=80
95% of the results between 1 and 12% yield

Figure 3B: Distribution of extraction yield of 55 experiments with 1% water

NORMAL distribution with water µ=9.1%, s=1.5
N=55
95% of the results between 6 and 12% yield

Figure 4: Effect of pH

Figure 5 shows the three covalently linked regions of an LPS molecule: (i) an O-specific polysaccharide chain (O-antigen) at the outer region; (ii) a core oligosaccharide central region; and (iii) lipid A.

Figure 6 shows truncated LPS produced by the mutant *S. minnesota* R595, and indicates the location of the truncation relative to full-length LPS.

LPS EXTRACTION PROCESS

This application is a divisional application of U.S. patent application Ser. No. 13/698,937 which was filed 19 Nov. 2012, under 35 U.S.C. §371 as a United States National Phase Application of International Patent Application Serial No. PCT/EP2011/058016 filed May 18, 2011, which claims priority to United Kingdom Application No. 1008401.0 filed May 20, 2010, the contents of which are incorporated herein by reference.

FIELD OF THE INVENTION

The present invention relates to the field of the biosynthetic production of lipopolysaccharide (LPS). Specifically, the present invention relates to improved methods and compositions for extraction of LPS from bacterial cells, such as cells obtained by bacterial cell culture. These methods and compositions of the invention are useful in the production of LPS, LPS derivatives and in particular, the production of 3-O-deacylated monophosphoryl lipid A (3D-MPL).

BACKGROUND

Figure 5:
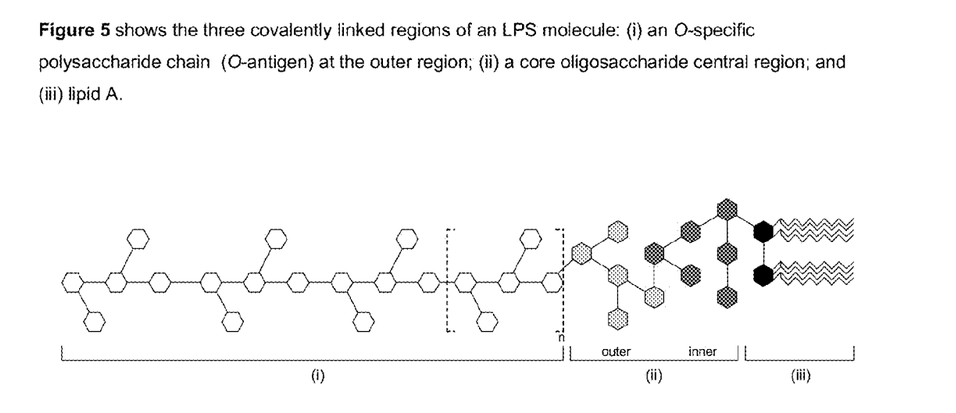
FIG. 5 shows the three covalently linked regions of an LPS molecule: (i) an O-specific polysaccharide chain (O-antigen) at the outer region; (ii) a core oligosaccharide central region; and (iii) lipid A.

Lipopolysaccharides (LPS) are the major surface molecule of, and occur exclusively in, the external leaflet of the outer membrane of gram-negative bacteria. LPS impede destruction of bacteria by serum complements and phagocytic cells, and are involved in adherence for colonisation. LPS are a group of structurally related complex molecules of approximately 10,000 Daltons in size and consist of three covalently linked regions (as shown in FIG. 5):
  (i) an O-specific polysaccharide chain (O-antigen) at the outer region
  (ii) a core oligosaccharide central region
  (iii) lipid A—the innermost region which serves as the hydrophobic anchor, it comprises glucosamine disaccharide units which carry long chain fatty acids.

SUMMARY OF THE INVENTION

It is an object of the present invention to provide compositions and methods for the extraction of LPS which result in improved bacterial yields of LPS. LPS yields may be calculated from the quantity of bacterial cells produced (biomass). Improved LPS yields enable greater quantities of LPS to be produced in a given facility, or for equivalent quantities of LPS to be produced using smaller facilities. A further object of the invention is to provide a process for the extraction of LPS that shows greater reliability and/or reproducibility of the yield of LPS extracted from the bacterial cells. A further object of the invention is to provide a faster process for the extraction of LPS.

Accordingly there is provided a method of lipopolysaccharide (LPS) extraction from gram negative bacterial cells comprising the step: extracting LPS from the cell membrane of bacteria using a composition (LPS extraction composition) comprising water, an alcohol and a further organic solvent.

DETAILED DESCRIPTION OF THE INVENTION

Known techniques of LPS extraction include the Galanos method, which involves extracting LPS with a mixture of phenol, chloroform, and petroleum ether (PCP), followed by evaporation of the chloroform and petroleum ether, addition of acetone and water to precipitate LPS, and recovery of LPS by centrifugation or filtration (Galanos et al., Eur. J. Biochem. 9: 245 (1969)). The Chen method involves extracting LPS with a mixture of chloroform and methanol (CM), followed by a series of methanol precipitation steps. The Galanos method is not suitable for commercial production of LPS, as it is not amenable to large scale production and uses solvent mixtures (e.g. phenol:chloroform:petroleum ether) that pose health and safety concerns. The Chen method results in a LPS- and phospholipid-rich CM phase which typically requires multiple precipitation steps to obtain LPS of sufficient purity for use in immunostimulatory applications such as, for example, use as a vaccine adjuvant. WO02/078637 discloses methods for the production of LPS and 3D-MPL using a deep rough mutant strain of gram-negative bacteria (in particular *Salmonella minnesota* R595). The methods of WO02/078637 show great variability in the yield varying from yields of 2% to 12%. Improved methods of LPS extraction are needed.

The inventors have shown that by using water in the LPS extraction step in addition to an alcohol and a further organic solvent, a greater LPS yield can be achieved compared to an equivalent process in which water is not used in the LPS extraction step. The present inventors have demonstrated that lipopolysaccharide can be extracted from gram negative bacteria by using an extraction composition comprising water yielding more LPS, with greater reliability and over a shorter period of time compared to equivalent compositions lacking water and without certain disadvantages associated with other extraction methods. In addition to an increased yield in LPS, the present inventors have shown that by using water in the LPS extraction composition (water, alcohol and organic solvent) this greater yield can be achieved with greater reliability and in less time than without water.

The term "LPS yield" as used herein means the amount of LPS obtained as a percentage of the dry bacterial cell weight (DCW).

Accordingly, there is provided a method of lipopolysaccharide (LPS) extraction from bacterial cells culture comprising the step of, extracting LPS from the cells using an LPS extraction composition comprising water, an alcohol and a further organic solvent. By "LPS extraction" or "extracting LPS from a bacterial cell" it is meant that the LPS is removed directly from the bacterial outer membrane.

In a further aspect of the invention there is provided an LPS extraction composition. By "LPS extraction composition" it is meant a composition/mixture used in the LPS extraction step wherein lipopolysaccharide is extracted directly from membranes of bacteria. The LPS extraction composition of the invention comprises water, an alcohol and a further organic solvent, and is useful in the LPS extraction methods of the invention. The LPS extraction composition of the present invention is a single-phase extraction composition. By "single phase" it is meant that the liquids form a single homogenous solution rather than a mixture wherein the liquids are immiscible.

The term "water" ($H_2O$) is well known to those in the art. The term encompasses pure and substantially pure water ($H_2O$) (including water obtained by distillation, de-ionization, ion-exchange treatment or reverse osmosis), and water comprising minor impurities as it is clear to the skilled person that water typically comprises some impurities. Water impurities are well known to those skilled in the art and include inorganic ions, organic molecules, particulates, colloids, dissolved gases, micro-organisms and their by-products. In a particular embodiment the water is sterile in that it is substantially in absence of any live micro-organisms. In a further embodiment, the water is filtered.

The present invention may further use aqueous solutions, for example water further comprising an alkali. In one embodiment, compositions of the invention do not comprise water in which an acid is dissolved. Accordingly, in one embodiment the pH of the water is neutral i.e. about pH 7. In one embodiment of the invention there is provided an LPS extraction composition comprising water, an alcohol, and an organic solvent, wherein the pH of the water is above 7. In a particular embodiment of the invention there is provided an LPS extraction composition wherein the pH of the LPS extraction composition is not below 7. In a particular embodiment, the pH of the water may be raised through the addition of one or more alkalis selected from the group: sodium hydroxide (NaOH), triethylamine (TEA) and potassium bicarbonate ($KHCO_3$).

The term "water" also encompasses deionized water. Deionized water is term well known to those skilled in the art, but briefly, deionised water is water in which substantially all mineral ions are removed. The level of deionization can be measured through conductivity and in a particular embodiment the deionized water has a maximum conductivity of 1 μsiemens/cm. The water of the invention does not have to be added separately from the other constituents of the LPS extraction composition. For example, the water in the LPS extraction composition may be derived from the alcohol solution comprising both alcohol and water and thus the skilled person needs only to mix the alcohol and the organic solvent to provide the LPS composition comprising an alcohol, an organic solvent and water.

As already stated, the present inventors have shown that the addition of water to extraction compositions comprising an alcohol and a further organic solvent, results in a greater LPS yield and/or greater consistency of LPS yield. Accordingly, there is provided an LPS extraction composition comprising water, an alcohol and a further organic solvent, wherein the amount of water in the LPS extraction composition is between about 0.1 and about 1.5% (v/v). LPS extraction compositions of the invention may comprise about 0.4% to 1.5% water (v/v), for example 0.4, 0.5, 0.6, 0.7, 0.8, 0.9, 1.0, 1.1, 1.2, 1.3, 1.4 or 1.5% (v/v). In particular, the amount of water in LPS extraction compositions of the invention is about 1% (v/v) i.e. between 0.8 to 1.2% (v/v).

LPS extraction compositions of the invention comprise an organic solvent in addition to an alcohol. The term "organic solvent" is well known in the art. Organic solvents are carbon-containing chemicals that are capable of dissolving a solid, liquid, or gaseous solute into a solution.

LPS extraction compositions of the invention comprise organic solvents which can be selected from the group: chloroform, alkanes, toluene and petroleum ether. Chloroform is well known to those skilled in the art and is represented by the chemical formula $CHCl_3$. Alkanes are also well known in the art. Alkanes are saturated hydrocarbons without any cyclic structure. LPS extraction compositions of the invention may comprise an alkane selected from the group: isooctane, ethane, heptane and hexane.

The percentage of organic solvent that is not an alcohol in the LPS extraction compositions of the invention can be between about 60% and about 95% (v/v) and in a particular embodiment of the invention the LPS extraction composition comprises between about 75% (v/v) and about 90% (v/v) solvent, in addition to the alcohol. LPS extraction compositions of the invention in particular comprise about 70, 71, 72, 73, 74 75, 76, 77, 78, 79, 80, 81, 82, 83, 84, 85, 86, 87, 88, 89 or 90% (v/v) solvent, in addition to the alcohol.

LPS extraction compositions of the invention comprise an alcohol. The term "alcohol" as used herein is defined as any acyclic organic compound in which a hydroxyl group (—OH) is bound to a carbon atom of an alkyl or substituted alkyl group. To clarify, aromatic non-saturated alcohols, such as phenol (a cyclic alcohol), are not encompassed by the present invention and thus there is provided an LPS extraction composition, comprising water, an alcohol and a further organic solvent, wherein the alcohol is not an aromatic non-saturated alcohol for example, phenol.

The percentage of alcohol in the LPS extraction compositions of the invention can be between about 5% and about 40% and in a particular embodiment of the invention the LPS extraction composition comprises between about 10% (v/v) and about 30% (v/v) alcohol. LPS extraction compositions of the invention in particular comprise 6, 7, 8, 9, 10 11, 12, 13, 14, 15, 16, 17, 18, 19, 20, 21, 22, 23, 24, 25, 26, 27, 28, 29 or 30% (v/v) alcohol.

The alcohol in the LPS extraction compositions of the invention can be selected from the list: isopropanol, methanol, ethanol, and butanol. The choice of alcohol may depend on a number of factors including the particular organic solvent in the particular LPS extraction composition in that certain alcohols are insoluble in certain organic solvents. Accordingly, in one embodiment of the invention there is provided an LPS extraction composition comprising water, chloroform and methanol. In an alternative embodiment of the invention there is provided an LPS extraction composition comprising water, an alkane and ethanol.

The LPS extraction compositions of the invention as defined herein are for use in the LPS extraction methods of the invention as described herein. Accordingly there is provided a method of lipopolysaccharide (LPS) extraction from bacterial cells comprising the step: extracting LPS from the cells in an LPS extraction composition as defined herein, comprising water, an alcohol and a further organic solvent. Methods of LPS extraction are well known to the skilled person.

Various parameters of the method of the invention may be altered whilst remaining within the scope of the invention, including temperature, time, and pH. Methods of the invention comprising the step of extracting LPS from cells (LPS extraction step) in an LPS extraction composition comprising water, an alcohol and a further organic solvent, may be performed at a temperature of between about 35° C. and about 65° C. In particular embodiments of the invention the LPS extraction step is performed at a temperature between about 45° C. and about 55° C., particularly 45, 46, 47, 48, 49, 50, 52, 52, 53, 54 or 55° C. In particular methods of the invention the extraction step is performed at about 50° C.

Methods of the invention may be performed comprising the step of extracting LPS from the cells in an LPS extraction composition comprising water, an alcohol and a further organic solvent, wherein the extraction step is performed at a pH between about 7 and about 9, for example about 7.1, 7.2, 7.3, 7.4, 7.5, 7.6, 7.7, 7.8, 7.9, 8.0, 8.1, 8.2, 8.3, 8.4, 8.5, 8.6, 8.7, 8.8 or 8.9. In particular embodiments of the invention the LPS extraction step is performed at a pH between about 7.8 and about 9 and in even more particular methods of the invention the extraction step is performed at about pH 8.6.

Methods of the invention comprising the step of extracting LPS from the cells in an LPS extraction composition comprising water, an alcohol and a further organic solvent, may be performed for about 0.5 to about 30 hours. In particular embodiments of the invention the LPS extraction step is performed for 1 to 20, particularly 0.5 to 1.5 1 to 2, 1.5 to 2.5 or 2 to 2.5 hours, for example 0.75, 1, 1.25, 1.5, 1.75, 2 or 2.25 hours. In particular methods of the invention the extraction step is performed for about an hour.

Methods of the invention may further comprise the steps: (i) washing cells with a solution of ethanol; and optionally (ii) washing a second time with ethanol. Washing with ethanol before the extraction step may reduce the amount of phospholipids that are co-extracted with the LPS in the LPS extraction step and thus washing can reduce the amount of impurities in the LPS extraction. Accordingly, there is provided a method of lipopolysaccharide (LPS) extraction from bacterial cells comprising the steps:
 (i) washing cells with a solution of ethanol;
 (ii) washing cells a second time with ethanol; and
 (iii) extracting LPS from the cells in an LPS extraction composition comprising water, an alcohol and a further organic solvent.

The washing steps in methods of the invention may be performed using a solution of between about 75% and about 95% (v/v) ethanol, the balance of the wash made with water. In certain embodiments of the invention the first wash (i) is performed with a solution of about 85% (v/v) ethanol. In further embodiment of methods of the invention the second wash (ii) is performed with a solution of about 90% (v/v) ethanol.

Further embodiments of methods of the invention may further comprise the step, washing cells with a solution of methanol. Accordingly, there is provided a method of lipopolysaccharide (LPS) extraction from bacterial cells comprising the steps:
 (i) washing cells with a solution of ethanol;
 (ii) washing cells a second time with ethanol;
 (iii) washing cells with methanol; and
 (iv) extracting LPS from the cells in an LPS extraction composition comprising water, an alcohol and a further organic solvent.

The methods of the invention are used to extract LPS from bacterial cells, including those obtained from bacterial cell cultures, so that the LPS can be used and/or further processed. Accordingly, further embodiments of the methods of the invention further comprise the step, evaporating the water, alcohol and further organic solvent from the LPS solution, thereby yielding a dry LPS residue following the extraction step. Suitably, there is provided a method of lipopolysaccharide (LPS) extraction from bacterial cells comprising the steps:
 (i) washing cells with a solution of ethanol;
 (ii) washing cells a second time with ethanol;
 (iii) washing cells with methanol;
 (iv) extracting LPS from the cells in an LPS extraction composition comprising water, an alcohol and a further organic solvent; and
 (v) evaporating the water, alcohol and further organic solvent from the LPS solution, thereby yielding a dry LPS residue.

In a further aspect of the invention there is provided an LPS composition produced by the methods of the invention. The biological activities of LPS, such as lethal toxicity, pyrogenicity and adjuvanticity, have been shown to be related to the lipid A moiety. In contrast, immunogenicity is associated with the O-specific polysaccharide component (O-antigen). Both LPS and lipid A have long been known for their strong adjuvant effects, but the high toxicity of these molecules has precluded their use in vaccine formulations. Significant effort has therefore been made towards reducing the toxicity of LPS or lipid A while maintaining their adjuvanticity.

The *Salmonella minnesota* mutant R595 was isolated in 1966 from a culture of the parent (smooth) strain (Luderitz et al. 1966 *Ann. N. Y. Acad. Sci.* 133:349-374). The colonies selected were screened for their susceptibility to lysis by a panel of phage, and only those colonies that displayed a narrow range of sensitivity (susceptible to one or two phage only) were selected for further study. This effort led to the isolation of a deep rough mutant strain which is defective in LPS biosynthesis and referred to as *S. minnesota* R595.

Figure 6:
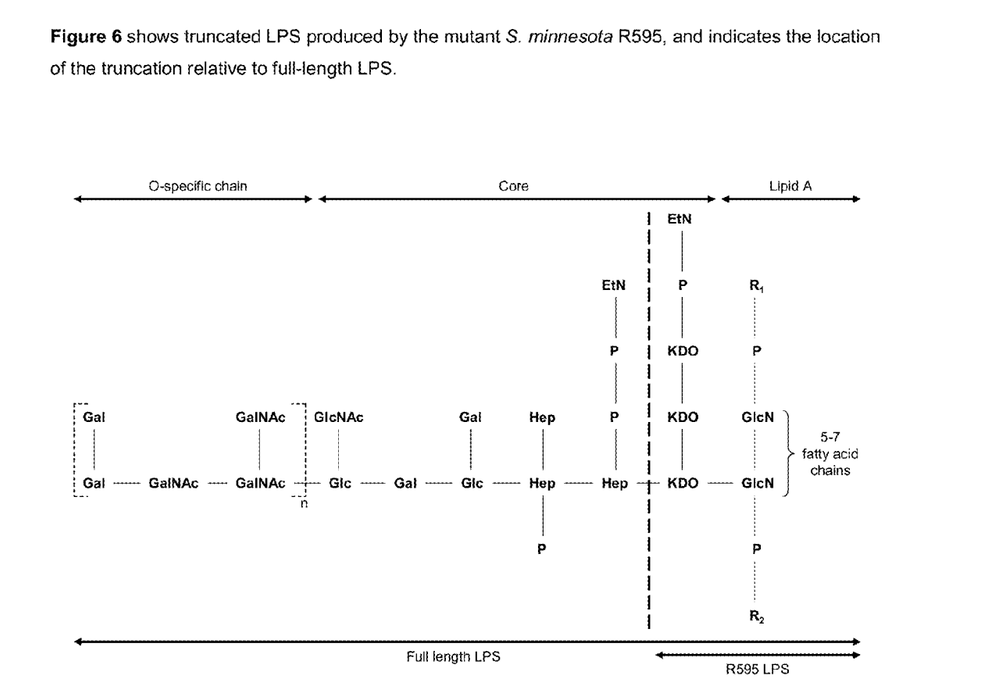
FIG. 6 shows truncated LPS produced by the mutant *S. minnesota* R595, and indicates the location of the truncation relative to full-length LPS.

In comparison to other LPS, those produced by *S. minnesota* R595 are truncated and have a relatively simple structure (see FIG. 6), as they:
 (i) contain no O-specific region—a characteristic which is responsible for the shift from the wild type smooth phenotype to the mutant rough phenotype and results in a loss of virulence
 (ii) the core region is very short—this characteristic increases the strain susceptibility to a variety of chemicals, and
 (iii) the lipid A moiety is highly acylated with up to 7 fatty acids.

Accordingly, the bacterial cells used in the methods of the invention may be that of a deep rough mutant bacterial strain of *Salmonella* or *Escherichia*. By the term 'deep rough mutant bacterial strain' is meant a strain of gram-negative bacterium having a deep rough phenotype. A deep rough phenotype is one wherein the polysaccharide moiety attached to the lipid A consists of only about 2-3 residues of 2-keto-3-deoxy-D-mannooctulonic acid (KDO). Particularly the deep rough mutant bacterial strain is selected from the genus *Salmonella*. If the deep rough mutant bacterial strain is selected from the genus *Salmonella*, it may be of the species *Salmonella minnesota*, in particular the strain *Salmonella minnesota* R595. Other deep rough mutant bacterial strains can be used, for example: *Compylobacter jejuni* (Kanipes et al. 2004 *Infection and Immunity* 72:2452-2455), *E. coli* K12 strain CS2429 (Klena et al. 2005 *J. Bact.* 187:1710-1715), *E. coli* D31m4 (Qureshi et al. 1988 *J. Biol. Chem.* 263:11971-11976), *E. coli* strain F515 (Wiese et al. 1997 *Biochemistry* 36:10311-10319) and Proteus mirabilis strain R45 (Wiese et al. 1997 *Biochemistry* 36:10311-10319).

4'-monophosporyl lipid A (MPL), which may be obtained by the acid hydrolysis of LPS extracted from a deep rough mutant strain of gram-negative bacteria, retains the adjuvant properties of LPS while demonstrating a toxicity which is reduced by a factor of more than 1000 (as measured by lethal dose in chick embryo eggs) (Johnson et al. 1987 *Rev. Infect.*

*Dis.* 9 Suppl:S512-S516). LPS is typically refluxed in mineral acid solutions of moderate strength (e.g. 0.1 M HCl) for a period of approximately 30 minutes. This process results in dephosphorylation at the 1 position, and decarbohydration at the 6' position, yielding MPL. 3-O-deacylated monophosphoryl lipid A (3D-MPL), which may be obtained by mild alkaline hydrolysis of MPL, has a further reduced toxicity while again maintaining adjuvanticity, see U.S. Pat. No. 4,912,094 (Ribi Immunochemicals). Alkaline hydrolysis is typically performed in organic solvent, such as a mixture of chloroform/methanol, by saturation with an aqueous solution of weak base, such as 0.5 M sodium carbonate at pH 10.5. Further information on the preparation of 3D-MPL is available in, for example, U.S. Pat. No. 4,912,094 and PCT publication WO02/078637 (Corixa Corporation).

Accordingly, methods of the invention may further comprise the step, subjecting the LPS to sequential acid hydrolysis and base hydrolysis, to form 3D-MPL and thus in a further embodiment of the invention there is provided a method of manufacturing an LPS derivative from gram negative bacteria comprising the steps:
 (i) washing cells with a solution of ethanol;
 (ii) washing cells a second time with ethanol;
 (iii) washing cells with methanol;
 (iv) extracting LPS from the cells in an LPS extraction composition comprising water, an alcohol and a further organic solvent;
 (v) evaporating the water, alcohol and further organic solvent from the LPS solution, thereby yielding a dry LPS residue; and
 (vi) subjecting the LPS to sequential acid hydrolysis and base hydrolysis, to form 3D-MPL.

In a further aspect of the invention there is provided 3D-MPL composition produced by methods of the invention as described herein.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The process of the present invention is illustrated by way of reference to the following non-limiting examples:

EXAMPLES

Example 1

LPS Extraction Process 1.1 Standard Washing Procedure (The Following Washing Process is Similar for Example 2)

This washing procedure is applied on cell broth 90A, 101B and 128A used in the following LPS extraction examples 1, 2 and 3.

A portion of inactivated broth (typically 200 L containing 3 to 5 kg DCW, 360 to 600 g LPS[1]) is charged in a 300 L double jacketed stainless reaction vessel with propeller, temperature probe, nitrogen blanketed and under 25 mbar of N2.

[1] Based on a maximum of 12% LPS content in the R595 cells assayed by the Galanos phenol total extraction method The broth is heated at 50° C. under stirring by circulating hot water in the double envelope of the reaction vessel.

The mixture is concentrated to 75 L by filtration (duration ~1.5 h) on a Tangential Flow Filtration (TFF) unit, fitted with a 7 channels cylindrical KERASEP® ceramic membrane of 0.22 μm pore size (6 mm Iinternal diameter) and 0.15 m2 surface area, Ref supplier: KERMBB-XM2 (Groupe Novasep France)). After analysis for dry weight residue and check that it is limpid, the permeate is discarded.

The retentate is diluted in ethanol (158 L) and water (18 L), yielding a total volume of 250 L. The mixture is heated at 50° C. and is post stirred 30 minutes at this temperature. The mixture is then concentrated till 50 L by tangential flow filtration (duration ~2 h) and the permeate is collected for analysis.

The retentate is further washed at 50° C. by addition of ethanol (180 L) and water (20 L) (duration ~2 h). Filtration to 50 L is performed after 30 minutes of post stirring. The permeates of both washes are analyzed for dry residue and discarded. Ethanol/water (~90/10) contained in the retentate is then replaced by methanol under dialysis mode at 50° C. on the TFF unit.

A total volume of 360 L of methanol, by 20 L fraction, is added to the retentate mixture while filtering the mixture, to yield a 50 L cell suspension in methanol (typical residual ethanol content <1%), substantially free of hydrophobic impurities (phospholipids) (duration ~3 h) Permeates is analyzed for dry residue and discarded.

Typically 20% of the total DCW is eliminated in the permeates during ethanol washes and replacement of ethanol by methanol steps. At this point the retentate mixture can be sampled to determine DCW and the material further processed at lab scale (137 ml) or pilot Plant scale (260 L).

1.2.2 Extraction Process (Pilot Plant Scale) without Water (as Performed for the Extraction of Broth 90B)

After washing steps as described above, (on 144 L of broth 90A containing 4 kg DCW), the 50 L washed cell suspension in methanol was extracted in Chloroform/Methanol. 190 L of chloroform and 20 L of Methanol was added. The mixture was further heated at 50° C. for 16 h. Grab samples were taken during the extraction and filtered. The amount of extracted LPS was then assayed by evaporating the solvent of the filtrate to allow yield calculation compared to the DCW measured on the broth.

The suspension was then filtered on the TFF unit and the permeate was sent to a 300 L stainless steel collection vessel, double jacketed, Nitrogen blanketed and under 25 mbar of N2. The permeate was cooled down by circulating cold water (8° C.) in the double jacket of the vessel.

When a residual volume of 50 L of retentate was obtained, the filtration was stopped (duration ~3 h)

1.3. Standard Concentration Procedure (Pilot Plant Scale Only)

The collected permeate (filtrate) is concentrated on a vacuum continuous-feeding rising tube evaporator (30° C., 200 mbar) until a volume of 17 L (minimum working volume of this equipment). Partial precipitation occurred during the evaporation, due to preferential evaporation of chloroform, and enrichment in methanol. Typical evaporation rate is 50-150 L/h, dependent on vacuum/condenser temperature (duration: 2-4 h).

The evaporator is emptied, and then washed with fresh chloroform (17 L) to solubilize any material precipitated during the evaporation.

The combined wash and concentrate (total volume: 34 L) is further evaporated on a 20 L Buchi ROTAVAPOR® R-220 (BÜCHI Labortechnik AG) with water bath at 50° C. and with an initial pressure of 350 mbar. Typical evaporation rate is 8-10 L/h (duration: 3-4 h).

When a volume of approximately 3 L is obtained, water (3 L) is added and the mixture is concentrated again to 3 L. This operation is repeated 2 times until a final pressure of 40 mbar is obtained, indicating that only water is remaining (all solvents being eliminated). During this methanol/water displacement, the typical evaporation rate is 2.5 L/h (typical duration ~3 h).

Another 3 L of water is added to yield ~6 L of LPS suspension in water, that is stored at 4° C., typically for 7 days. The suspension is sampled and analysed for dry residue, in order to estimate the LPS quantity (also called CME, Chloroform/Methanol exstract) quantity:

Yielding 189 g of LPS for the extraction of broth 90A.

Figure 3A:
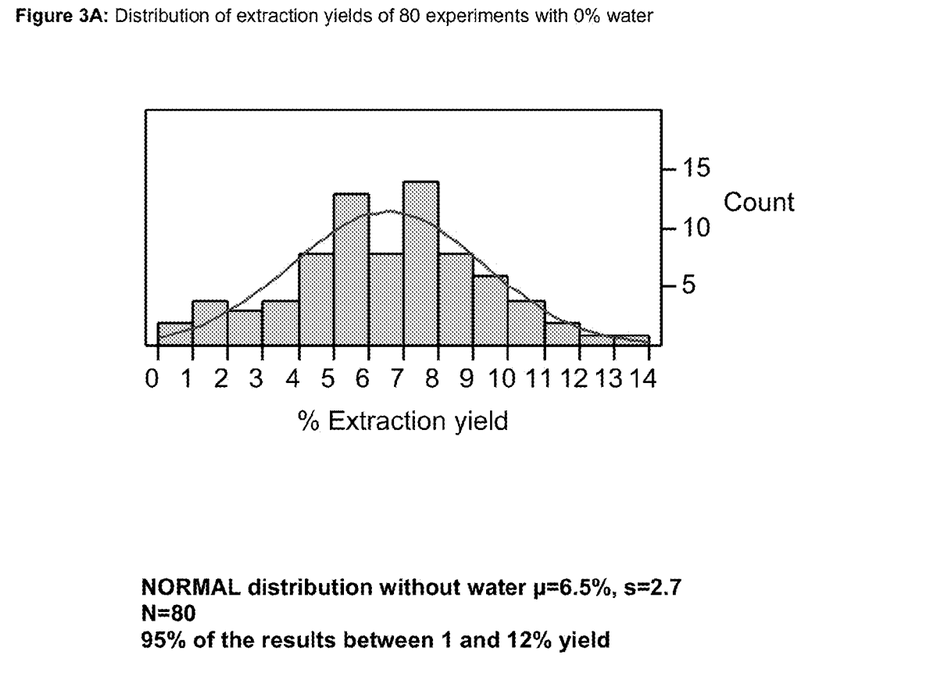
FIG. 3A: Distribution of extraction yields of 80 experiments with 0% water

The average yield of the N=80 experiment performed with 0% water during extraction (see FIG. 3) is 6.5%, showing a very broad distribution, with 95% of results between 1 and 12% yield.

Example 2

Extraction Using Water

The washing of cells, 222 L from broth 131A containing 5 kg DCW was performed as described section 1.1.

2.1 Method 2.1.1 Extraction (Pilot Plant Scale with 1% Water) (as Performed for Extraction of Broth 131A)

Chloroform (195 L) and water (2.5 L) was added to the washed R595 cells (50 L in methanol) to give a solvent ratio of 78/22/1 CHCl3/MeOH/H2O. The mixture was heated at 50° C. and post stirred overnight (16 h) at this temperature.

The suspension was then filtered on the TFF unit and the permeate was sent to a 300 L stainless steel collection vessel, double jacketed, Nitrogen blanketed and under 25 mbar of N2. The permeate was cooled down by circulating cold water (8° C.) in the double jacket of the vessel.

When a residual volume of 50 L of retentate was obtained, the filtration was stopped (duration ~3 h). Chloroform (40 L) and methanol (10 L) was added to the retentate for further extraction and the mixture was re-heated at 50° C. and filtered until a volume of 50 L. The additional 50 L of permeate was also sent to the collection vessel. The remaining 50 L of retentate was then discarded.

The concentration was performed as described in section 1.3, yielding 568 g of LPS.

Figure 3B:
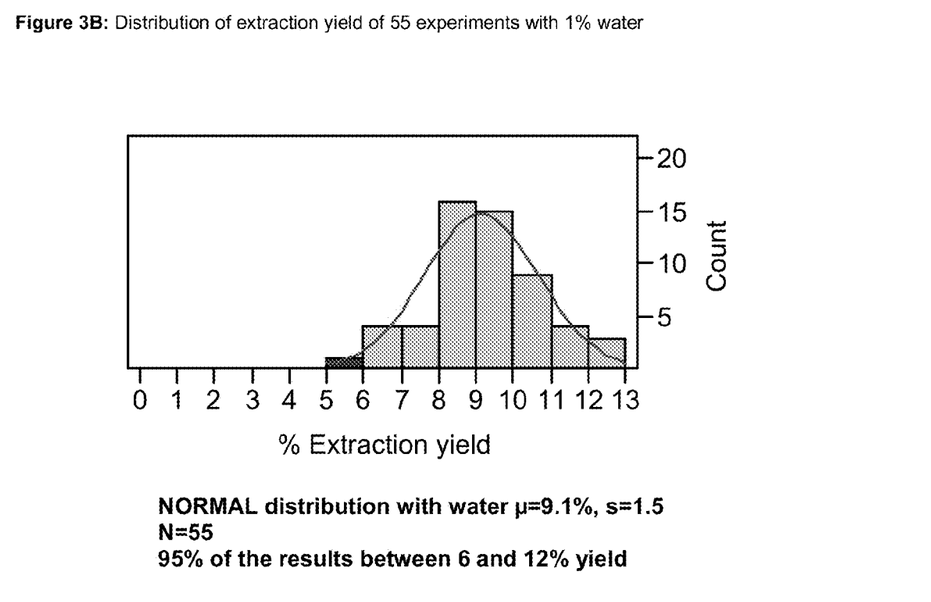
FIG. 3B: Distribution of extraction yield of 55 experiments with 1% water

The average yield in these conditions is 9.1% with 95% of the results comprised between 6 and 12% yield as shown in FIG. 3.

Example 3

Lab Extraction with and without Water

130 L of inactivated broth 101B (2.99 kg DCW) was washed using the procedure described in 1.1, yielding 50 L of washed cells. Washed cells were sampled for scale downed lab extractions.

In order to better understand the extraction process, this step was scaled down and different extraction conditions were tested and kinetics up to 48 h extraction was established. Washed cells from broth 101B were used for those experiments.

To 30 ml of a washed R595 cell suspension in methanol was added 106 ml of chloroform and if needed 1.36 ml of water in a round bottomed flask equipped for the reflux and under inert atmosphere of nitrogen. The suspension was stirred at 50° C. Grab samples (10 ml) were taken during the extraction (up to 48 h) and filtered on 0.22 μm polytetrafluoroethylene (PTFE) filter. The filtrate was evaporated until dry to determine the amount of extracted LPS and follow kinetic of extraction. Yield was calculated from total experiment Volume×LPS content divided by DCW of the original broth.

2.2 Results

Table 1 shows that effect on yield of 1% water in the chloroform:methanol extraction buffer.

TABLE 1

Effect of water on LPS content during extraction (performed at PP scale in 16 h at 50° C.)

| Cell broth Lot N° | Volume inac broth | % Water | LPS in CME (g) | Yield % (LPS/DCW from broth) |
|---|---|---|---|---|
| 90A | 144 L (4 KgDCW) | 0 | 189 | 4.7 |
| 131A | 222 L (5 Kg DCW) | 1 | 568 | 11.4 |

It can be seen that the LPS content following extraction using 1% water (131A) was significantly increased, compared to the LPS content following extraction using 0% water (90A).

Figure 1:
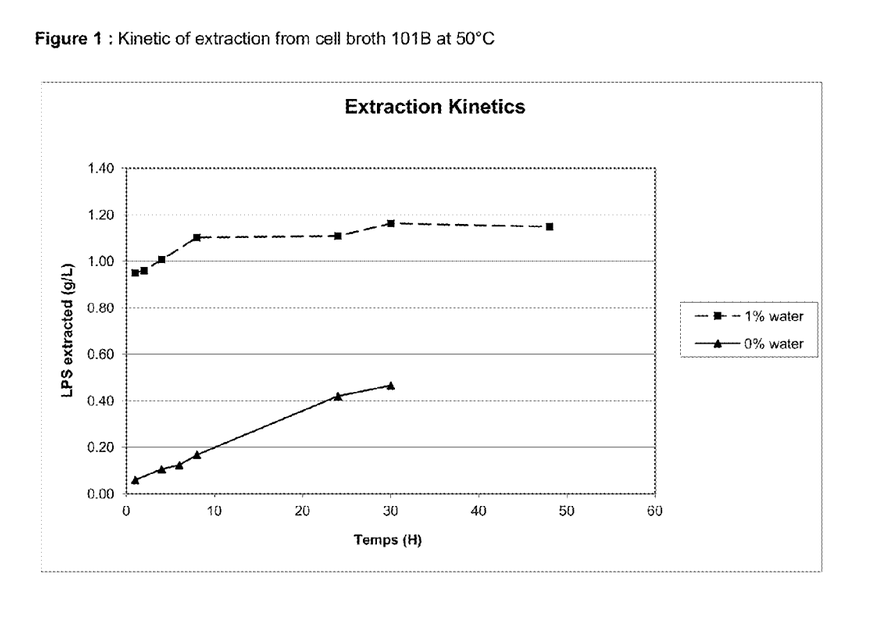
FIG. 1 Kinetic of extraction from cell broth 101B at 50° C.
Figure 2:
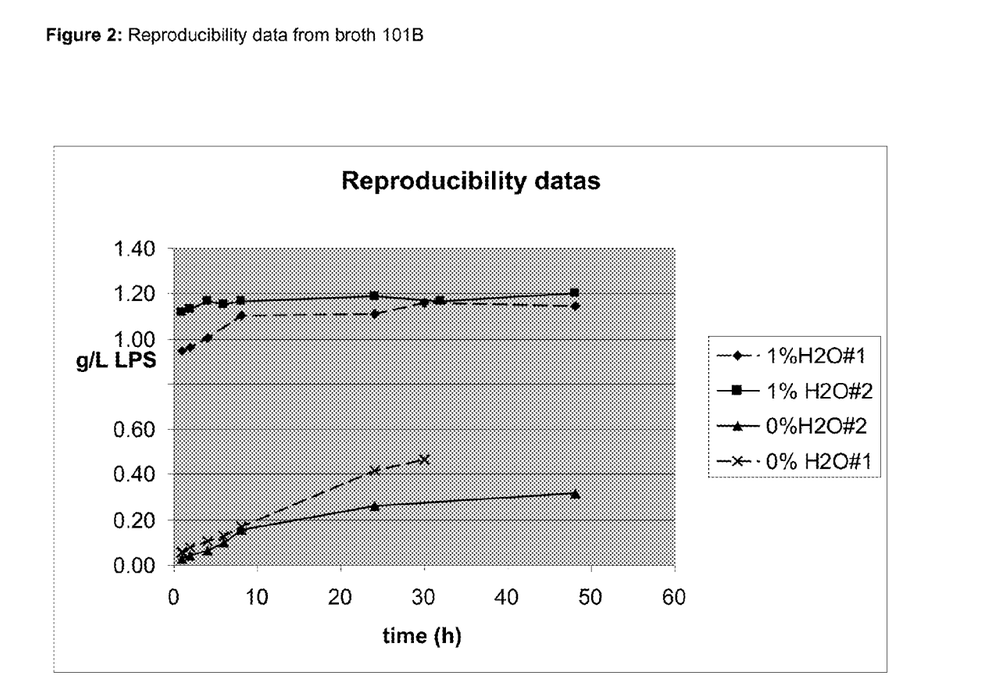
FIG. 2 Reproducibility data from broth 101B

Kinetics:

In addition to an increase in LPS yield, the examples demonstrate that the addition of water to the extraction buffer increased the kinetic of extraction (see FIG. 1 and FIG. 2, lab scale experiment from cell broth 101B)

It is shown that after 8 hours a plateau (1.15 g/l) was reached in extraction performed with 1% water present. However, in the absence of water only 0.17 g/L was dissolved after 8 hours—after 30 hour the amount was 0.47 g/L (and was still growing, to an hypothetical high value, but after a long time).

These experiments were repeated twice on the same broth (101B). Sample was taken after 1 h, 2 h, 4 h, 8 h, 24 h, 30 h and 48 h of extraction.

Reproducibility:

In addition to the yield and speed with which LPS may be extracted, 1% water also increased the reproducibility with which LPS is extracted (see FIGS. 3A & 3B and 2).

It is shown in FIG. 3 that distribution and standard deviation are sharpened with 1% water.

It is shown in table 2 that reproducibility is improved using 1% water; when using 0% water a 40% difference is observed between yields obtained from the $1^{st}$ and $2^{nd}$ trial.

TABLE 2

Extractions % Yield 50° C. 0% and 1% water at lab scale,
samples taken after 1 h and 30 h (from cell broth 101B).

| Lot | Water | Extraction time | LPS g/L (in 137 ml) | Yield (from LPS/DCW broth 101B)* |
|---|---|---|---|---|
| #1 | 1% | 1 h | 0.95 | 7.3% |
|  |  | 30 h | 1.16 | 8.9% |
| #2 | 1% | 1 h | 1.12 | 8.4% |
|  |  | 30 h | 1.17 | 8.9% |
| #1 | 0% | 1 h | 0.05 | 0.4% |
|  |  | 30 h | 0.45 | 3.4% |
| #2 | 0% | 1 h | 0.03 | 0.2% |
|  |  | 30 h | 0.26 | 2% |

*Based on an equivalence of 1794 mg DCW (2.99 kg/50 L/30 ml) × 1000) from broth 101B sampled for each extraction experiment Example 3

Effect of pH

130 L of inactivated broth 101B (2.99 kg DCW) was washed using the procedure described in 1.1, yielding 50 L of washed cells. Washed cells were sampled for scaled down lab extractions.

120 ml of chloroform and 1.5 ml of water was added to 25 ml of a washed cell suspension in methanol containing the desired base (e.g. 15.15 mg of TEA, 50 mg of KHCO3, 25 µl NaOH 32%) in a round bottomed flask equipped for the reflux and under inert atmosphere of nitrogen. The suspension was stirred at 50° C. for 16-18 h. A sample (10 ml) was taken and filtered on 0.22 µm PTFE filter. The filtrate was dried by evaporation to determine the amount of extracted LPS (g/L).

The effect of pH was tested at pH 8.61 (NaOH), 8.29 (TEA), 7.84 (KHCO3) and pH4 (acetic acid).

Results were compared with extraction with 1% water at pH=7.1.

Elevation of the pH was obtained by dissolving 1.6 equivalent of the desired base (based on 12% LPS content) in the amount of water used to reach the 1% ratio C:M:W. The aqueous solution was added to the methanolic suspension and stirred 1 h before the addition of $CHCl_3$ and heating at 50° C. In the case of acetic acid, the acid was added directly to the methanol water mixture.

Figure 4:
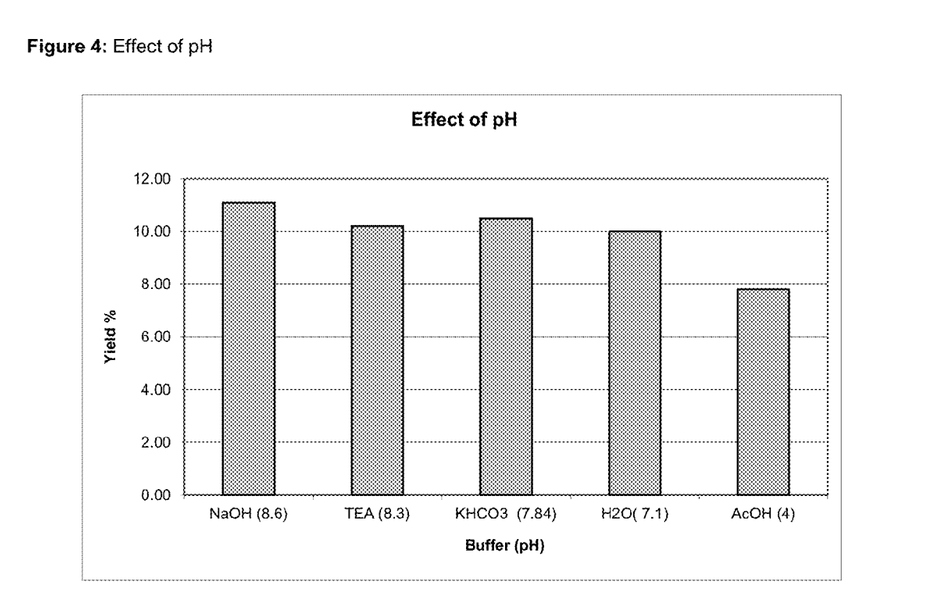
FIG. 4 Effect of pH

In is shown in FIG. 4 that LPS yield increased with the pH, from 7.8% at pH 4 (acetic acid) to 11.1% at pH 8.6 (NaOH). (N.B. the increase of dry content due to the addition of KHCO3 and NaOH was taken into account for the yield calculation. TEA and acetic acid was eliminated by evaporation if still present.

4. Conclusion

The present inventors have demonstrated that addition of water generates more reliable extraction condition (reproducibility) and increases the LPS yield.

Moreover the inventors have shown that an increase in the pH of the aqueous extraction buffer increases the LPS yield.

The invention claimed is:

1. A method of lipopolysaccharide (LPS) extraction from gram negative bacterial cells comprising the step, extracting LPS from the gram negative bacterial cells in an LPS extraction composition comprising water, an alcohol and a further organic solvent, wherein the LPS extraction composition is single-phase, and wherein the amount of water in the LPS extraction composition is between about 0.8 to 1.2% (v/v).

2. The method of claim 1 wherein the extraction of LPS is performed at a temperature of between about 35° C. and about 65° C.

3. The method of claim 1 wherein LPS extraction is performed at a pH of between 7.8 and 9.

4. The method of claim 1 wherein the LPS extraction is performed in about 0.5 to about 20 hours.

5. The method of claim 1 further comprising the steps:
   i. Washing cells with a solution of ethanol or methanol prior to the step of extraction; and optionally
   ii. Washing cells a second time with ethanol or methanol prior to the step of extraction.

6. The method of claim 1 further comprising the step: evaporating the water, alcohol and further organic solvent from the LPS solution, thereby yielding a dry LPS residue.

7. The method of claim 1 further comprising the step: subjecting the LPS to sequential acid hydrolysis and base hydrolysis, to form 3D-MPL.

8. The method of claim 1 wherein the amount of water is about 1% (v/v).

9. The method of claim 1 wherein the alcohol is selected from the list: methanol, ethanol, isopropanol or butanol.

10. The method of claim 1 wherein the percentage of alcohol in the LPS extraction composition is between about 5% and about 40% (v/v).

11. The method of claim 1 wherein the LPS extraction composition comprises chloroform, methanol and water.

12. The method of claim 1 wherein the LPS extraction composition comprises an alkane, ethanol and water.

* * * * *